US010285398B2

(12) United States Patent
Świętoslawski

(10) Patent No.: US 10,285,398 B2
(45) Date of Patent: May 14, 2019

(54) MOLLUSCICIDE COMPOSITION

(71) Applicant: ICB PHARMA SPÓŁKA JAWNA, Jaworzno (PL)

(72) Inventor: Janusz Świętoslawski, Jaworzno (PL)

(73) Assignee: ICB Pharma Spolka Jawna, Jaworzno (PL)

(*) Notice: Subject to any disclaimer, the term of this patent is extended or adjusted under 35 U.S.C. 154(b) by 0 days.

(21) Appl. No.: 15/317,874

(22) PCT Filed: Jun. 10, 2014

(86) PCT No.: PCT/PL2014/000061
§ 371 (c)(1),
(2) Date: Dec. 9, 2016

(87) PCT Pub. No.: WO2015/126267
PCT Pub. Date: Aug. 27, 2015

(65) Prior Publication Data
US 2017/0135338 A1 May 18, 2017

(51) Int. Cl.
A01N 25/00 (2006.01)
A01N 37/44 (2006.01)
A01N 55/02 (2006.01)

(52) U.S. Cl.
CPC .......... *A01N 25/008* (2013.01); *A01N 37/44* (2013.01); *A01N 55/02* (2013.01)

(58) Field of Classification Search
None
See application file for complete search history.

(56) References Cited

U.S. PATENT DOCUMENTS

| 3,090,723 | A | 5/1963 | Pastac |
| 4,251,946 | A | 2/1981 | Lindley |
| 5,437,870 | A | 8/1995 | Puritch et al. |
| 6,447,794 | B2 | 9/2002 | Young |
| 6,703,036 | B1 | 3/2004 | Young |
| 7,431,743 | B2 * | 10/2008 | Hughes ............... C09B 67/0073 8/506 |
| 2007/0148203 | A1 | 6/2007 | Parker et al. |

FOREIGN PATENT DOCUMENTS

| AU | 689399 | 3/1998 |
| AU | 697781 | 10/1998 |
| AU | 735902 | 7/2001 |
| EP | 1752043 | 2/2007 |
| JP | 2004026662 | 1/2004 |
| PL | 223820 | 11/2016 |
| WO | 8901287 | 2/1989 |
| WO | 9726789 | 7/1997 |
| WO | 9939576 | 8/1999 |
| WO | 02/09518 | * 2/2002 |
| WO | 02063960 | 8/2002 |
| WO | 03069996 | 8/2003 |
| WO | 03079781 | 10/2003 |
| WO | 2004075634 | 9/2004 |
| WO | 2009/048345 | * 4/2009 |
| WO | 2009048345 | 4/2009 |
| WO | 2015/126267 A1 | 8/2015 |

OTHER PUBLICATIONS

Database CAPLUS Chemical Abstracts Service, Columbus, Ohio, US; Database Accession No. 1992:464804, Abstract of Anya, Discovery and Innovation (1992), 4(1), 67-9 (Anya) or CN 02115724.*
Machine Translation of CN 02115724 (2003), retrieved from internet May 11, 2017, retrieved from URL: https://patents.google.com/patent/CN1451277A/en.*
CN 102816006 (2012) Machine Translation retrieved Aug. 22, 2017 from url: https://patents.google.com/patent/CN102816006A/en.*
Steinberg et al., Internat. Rev. Hydrobiol. 87 2002 1 121-133 (Year: 2002).*
Desouky, "Amelioration of behavioural toxicity of aluminum by oligomeric silicic acid and humic acid," Egyptian Journal of Biology, 2001, pp. 56-62, vol. 3.
International Search Report and Written Opinion from related International Application No. PCT/PL2014/000061, dated Sep. 5, 2014, 9 pgs.
English translation of CN102816006A.
I. F. Henderson, et al., "Control of slugs with contact-action molluscicides", Association of Applied Biologists, Feb. 26, 1990, pp. 273-278.

* cited by examiner

Primary Examiner — Karl J Puttlitz
(74) Attorney, Agent, or Firm — Ware, Fressola, Maguire & Barber LLP

(57) ABSTRACT

The present invention relates to a molluscicide composition having a form of food bait and comprising at least one molluscicidal agent. In order to improve efficacy and ecological properties of a molluscicide it further comprises humic acid. The invention also relates to a method of preparing such a composition, a molluscicide dosage form comprising such a composition, as well as a method and use of such a molluscicide composition or a molluscicide dosage form in combating molluscs for an extended period in agricultural, horticultural and/or garden environments.

10 Claims, No Drawings

MOLLUSCICIDE COMPOSITION

The present invention relates to a molluscicide composition having a form of food bait and comprising at least one molluscicidal agent. The invention also relates to a method of preparing such a composition, a molluscicide dosage form comprising such a composition, as well as a method and use of such a molluscicide composition or a molluscicide dosage form in combating molluscs for an extended period in agricultural, horticultural and/or garden environments.

BACKGROUND OF THE INVENTION

Molluscs, especially slugs and snails are known to cause severe plant damages by feeding on them during the entire season of plant vegetation and especially in months with a large quantity of rainfalls and relatively low temperatures. Various molluscicides have been proposed in the state of art for combating snails and slugs featuring various efficacy and properties.

In general molluscicides may be divided into three groups. These are contact-action molluscicides, such as aluminium and copper sulphate crystals, which are applied to the area inhabited by molluscs and adhere to snails or slugs moving in this area; irritant powder molluscicides, such as silica grains, which act by being taken up in the snail's or slug's locomotion mucus; and stomach-action molluscicide baits which are ingested by molluscs.

Most of the molluscicide baits are delivered in a form of granulated pellets to be scattered over the entire field or only in the specified centres of molluscs' occurrence. Application should usually be repeated during the season since in a given moment the pests usually exist simultaneously in different phases of their growth and development.

Molluscicide bait is usually a composition containing at least one molluscicidal agent and a feed bait base.

Common molluscicidal agents include metal chelates, metaldehyde and methiocarb. One of the safest and ecological stomach-action method for combating molluscs involves molluscicidal agents in the form of salts or chelates of iron (III) (cf. Henderson, et al. Crop Protection, 9, 131-134, (1990), WO 89/01287, U.S. Pat. Nos. 5,437,870, 6,447,794, 6,703,036, EP 1752043, WO 03/069996, WO 03/079781, US 2007/0148203, WO 97/26789, WO 2004/075634, AU 689399, AU 697781, AU 735902, PL 195194). Exemplary preparations of this kind which are commercially available include Ferramol® and Sluggo® (containing iron (III) phosphate and EDTA and/or EDDS) or Multiguard® (containing 6% of Fe(III)EDTA chelate).

International publications WO 2009/048345, as well as Polish patent application P. 396674 also disclose molluscicide bait comprising iron powders and/or iron alloys powders as molluscicidal agent, at least one complexing agent; and molluscs' edible agent. Preferred complexing agents are ethylenediaminetetraacetic acid (EDTA) or methylglycinediacetic acid (MGDA) and/or mixtures thereof with other, particularly biodegradable, complexing agents. Such a mixture of iron powder and EDTA forms iron(II) EDTA chelate in situ only after it reaches the molluscs gut.

Common feed bait bases include starch matrix like cereal meals, preferably with bran, sugar, yeast (cf. publications U.S. Pat. Nos. 3,090,723, 4,251,946), fish meal or phagostimulants (cf. EP 1752043).

Furthermore molluscicide baits may contain other constituents including but not limited to substances against mould growth such as IPBC, DCOIT or sorbic acid; alerting (aversive) agents such as Bitrex®; rain-resistance improving agents; granulate extrusion process improving agents such as kaolinite or modified starch; additional attractants such as red clover, paraldehyde, isoamyl acetate, 2-methyldecanol (cf. JP 2004026662) or sulfur compounds (cf. WO 2002/063960); and other known additives.

The object of the present invention has been to provide molluscicide having a form of food bait which would be more efficient and economically reasonable than known molluscicide compositions, harmless to other animals and free of unwanted side-effects.

The inventor unexpectedly discovered that addition of a humic acid to a molluscicide composition displays excellent efficiency in attracting and combating molluscs.

SUMMARY OF THE INVENTION

Accordingly the invention provides a molluscicide composition having a form of food bait and comprising at least one molluscicidal agent which is characterized in that it further comprises humic acid.

Humus constituting a mixture of humic substances, inorganic matter, carbohydrates and microorganisms is important in the diet of molluscs (cf. J. Perea, at. Al., "Book of Abstracts of $57^{th}$ Ann. Meeting of Eur. Assoc. Anim. Prod.", Antalya, Turkey, 2005, pp. 157).

Humic substances are the major organic constituent not only of humus (soil) but also of peat, coal, and various unplanted streams, produced by biodegradation of dead organic matter. Humic substances can be divided into three main fractions: humic acids, fulvic acids, and humin.

Humic acids have a form of mixtures of many different acids containing carboxyl and phenolate groups, which is not soluble in water under acidic conditions (high molecular weight). Fulvic acids are humic substances that are soluble in water in all pH conditions (low molecular weight). Humins are a class of organic compounds that are insoluble in water at all pH conditions.

Humic and fulvic acids may be extracted as a colloidal sol from soil and other solid phase sources in strongly basic aqueous solution of sodium hydroxide or potassium hydroxide. Humic acids are precipitated from this solution by adjusting the pH to 1 with hydrochloric acid, leaving the fulvic acids in solution. This is the operational distinction between humic and fulvic acids. Humin is insoluble in dilute alkali.

Although all the above captioned substances are constituents of natural molluscs diet the inventor unexpectedly discovered that only humic acids display excellent attractant properties, whereas fulvic acids act as strong repellents.

These excellent attractant properties of humic acids enables for using significantly decreased contents of molluscicidal active agents, what is of particular importance in case of toxic molluscicidal agents such as metaldehyde.

Furthermore humic acids are commonly used in agriculture as soil supplements to improve the buffering power and regulate the pH value of the soil, stimulate the growth of the plants, increase the yield and quality of plants. Therefore the inventive attractant proposed according to the invention is not only very effective in combating molluscs but also beneficial to plants. Therefore the remnants of the molluscicide composition not digested by molluscs are not only harmless but also fertilize the soil.

Preferably the molluscicide composition comprises comprise from 1 to 30% by weight of humic acid.

Preferably said molluscicidal agents are selected from the group containing metaldehyde, methiocarb, metal chelates, iron powder, ethylenediaminetetraacetic acid (EDTA), methylglycinediacetic acid (MGDA) and/or mixtures thereof in all ratios.

Even more preferably said molluscicidal agents include EDTA acid and iron powder, preferably the composition contains up to 10% by weight of EDTA acid and up to 5% by weight of iron powder and even more preferably from 2 to 5% by weight of EDTA acid and from 0.5 to 2% by weight of iron powder.

Preferably the composition further comprises plant materials, in particular containing starch, preferably wheat or corn meal or potato starch or mixtures thereof in all ratios.

Preferably the composition further comprises one or more of the following constituents:
- substances against mould growth, such as IPBC, DCOIT and/or sorbic acid;
- alerting (aversive) agents such as Bitrex®;
- rain-resistance improving agents;
- granulate extrusion process improving agents such as kaolinite and/or modified starch;
- synthetic or natural fertilizers such as urea and/or humus,
- additional attractants, such as red clover, yeast, sugar, paraldehyde, isoamyl acetate, 2-methyldecanol, and/or sulfur compounds.

The composition according to the invention has preferably a form of a grain, a pellet, a granule, a powder, a capsule, a solution, a dispersion and a paste, with a pellet and a granule being more preferred.

Granules may conveniently be formed in a roll compaction machine, in a noodle making device or in an extruder. Extruding process may further lead to gelation (temperature between 65 to 95° C.) of the starch contained in the mixture and therefore the resultant granulate features significant rain- and mechanical-resistance.

The invention also provides a method of preparing a molluscicidal composition, wherein the components are mixed and the mixture is appropriately converted to the form as above, as well as a molluscicide dosage form as above.

The invention also provides a method for mollusc control, in which the molluscicide composition or the molluscicide dosage form as defined above, preferably at rates of between 0.1 g/m$^2$ to 10 g/m$^2$, preferably in the form of pellets and/or granules, is applied to a field infested, or likely to become infested, with molluscs, over the entire field or only in the specified centers of molluscs' occurrence, wherein the application is optionally repeated during the season as necessary.

The invention finally provides a use of the molluscicidal composition or dosage form as defined above in combating molluscs for an extended period in an agricultural, horticultural or garden environment.

DETAILED DESCRIPTION OF THE INVENTION

The following non-limiting examples serve to further illustrate the present invention. They should not however be considered as exhaustive or limiting the scope of the invention applicability and the scope of intended protection as defined by the appended patent claims.

The constituents used and described in the following examples had the following origin.

Ferronyl Iron® manufactured by International Specialty Products Inc. (ISP, New Jersey, USA) was used as an iron powder. Ferronyl Iron® is not a reduced elemental iron but an elemental iron obtained by chemical decomposition of iron pentacarbonyl. The resulting powder contains small, spherical iron particles of excellent purity.

Metaldehyde (99%) was manufactured by Lonza Group Ltd (Switzerland).

Humic acid (85%), fulvic acid (70%), potassium humate (75% humic acid+12% $K_2O$) were manufactured by Shandong Chuangxin Humic Acid Technology Co., Ltd (PRC).

Example I

Compositions A, B, C and D have been prepared in a pasta shaping machine LaMonterrina, Type P3• according to the standard procedure and shaped to a form of cut granulates having diameter of 2.3 mm. Table I.1 lists the contents of dried granulated compositions. Granulate A has been prepared according to Example III (F) of the publication WO 2009/048345 as a comparative formulation. As shown all granulates contained the same type and quantity of an active agent.

TABLE I.1

| Molluscicide granulated baits | | | | | |
|---|---|---|---|---|---|
| | | Granulate composition [% by weight] | | | |
| Constituent | | A | B | C | D |
| Molluscicidal agent | EDTA acid | 3.9 | 3.9 | 3.9 | 3.9 |
| | Ferronyl Iron ® | 1.0 | 1.0 | 1.0 | 1.0 |
| Humic substance | Humic acid | — | 10.0 | — | — |
| | Fulvic acid | — | — | 10.0 | — |
| | Potassium humate | — | — | — | 10.0 |
| Feed bait base & additional constituents | Wheat meal, east, sugar, modified starch, sorbic acid | Up to 100% | | | |

Molluscicide efficacy of granulates A-D has been examined in four aquariums (25×40×40 cm), each containing wet soil layer of thickness amounting 5 cm, lettuce leaf and a container with drinkable water. Each granulate A-D has been evenly spread in dose of 2 g per aquarium on the bottom of the aquarium corresponding to this granulate. Tests have been performed in a room temperature and animals were classified as active (ACT), knocked down (KD) or dead (D) at each assessment.

Observed mortality was calculated as:

$$M=(KD+D)/(ACT+KD+D)$$

Observed lettuce damage was calculated as a percentage of eaten leaf area.

Table I.2 shows the results of the tests conducted on the population of *Deroceras reticulatum* and *Arion lusitanicus* slugs (10+10 animals per aquarium) respectively after two and five days.

TABLE I.2

| Efficacy comparison (*Deroceras reticulatum* and *Arion lusitanicus*) | | | | |
|---|---|---|---|---|
| Granulate composition | A | B | C | D |
| Days (DAT) | 2 (5) | 2 (5) | 2 (5) | 2 (5) |
| Observed mortality M [%] | 20 (80) | 60 (100) | 0 (40) | 0 (45) |
| Observed lettuce damage [%] | <20 | <10 | <20 | <20 |

Table I.3 shows the results of the tests conducted on the population of *Helix aspersa* snails (10 big snails per aquarium) respectively after two and seven days.

TABLE I.3

Efficacy comparison (*Helix aspersa*)

| Granulate composition | A | B | C | D |
|---|---|---|---|---|
| Days (DAT) | 2 (7) | 2 (7) | 2 (7) | 2 (7) |
| Observed mortality [%] | 20 (80) | 60 (100) | 0 (15) | 0 (30) |
| Observed lettuce damage [%] | <10 | <10 | <20 | <20 |

Test results listed in Tables I.2 and I.3 clearly indicate a better efficacy of granulate B (containing humic acid) comparing to granulate A. Tables I.2 and I.3 also clearly show repellent properties of humic substances other than humic acid contained in granulates C and D. Addition of water soluble fulvic acid (C) or potassium humate (D) significantly decreased efficacy even with regard to the base comparative formulation (A) entirely devoid of humic substances. No knocked down or dead animals have been observed after the first two days of the tests for granulates C and D.

Example II

Compositions E, F, G and H have been prepared in an extruding machine (85° C.) according to the standard procedure with a diameter of 2 mm. Table II.1 lists the contents of these granulated compositions after drying.

TABLE II.1

Molluscicide granulated baits

| | Constituent | E | F | G | H |
|---|---|---|---|---|---|
| Molluscicidal agent | EDTA acid | 3.9 | — | — | — |
| | Ferronyl Iron ® coated with ascorbic acid 6-palmitate and alpha-tocopherol | 1.0 | — | — | — |
| | Metaldehyde | — | 4.0 | 2.0 | 1.0 |
| Humic substance | Humic acid | 5.0 | — | 5.0 | 5.0 |
| Feed bait base & additional constituents | Wheat meal, east, sugar, modified starch, sorbic acid | Up to 100% | | | |

Molluscicide efficacy of granulates E to H has been examined in four aquariums prepared as described in Example I and according to the procedure described therein.

Table II.2 shows the results of the tests conducted on the population of *Helix aspersa* snails (10 big snails per aquarium) respectively after two and four days.

TABLE II.2

Efficacy comparison (*Helix aspersa*)

| Granulate composition | E | F | G | H |
|---|---|---|---|---|
| Days (DAT) | 2 (4) | 2 (4) | 2 (4) | 2 (4) |
| Observed mortality [%] | 70 (100) | 70 (80) | 90 (100) | 75 (85) |
| Observed lettuce damage [%] | <10 | <10 | <10 | <10 |

Test results clearly indicate excellent features of the humic acid as an attractant. After four days there were still active snails in an aquarium containing composition devoid of humic acid (F). Also composition G containing lesser amount of metaldehyde (2% by weight) but with an addition of humic acid proved to be significantly more effective than composition F containing as much as 4% by weight of metaldehyde but devoid of humid acid. The results also indicate excellent efficacy of compositions without metaldehyde which is a toxic molluscicidal agent also harmful to dogs and other domestic animals.

Example III

A small plot replicated field trials were conducted to evaluate efficacy of granulates E and A with reference to "DEFENDER Snail and Slug Pellets" (Scotts Australia Pty Ltd) bait containing metaldehyde molluscicidal agent in an amount of 15 g/kg and MULTICROP MULTIGUARD® Snail and slug killer (Multocrop Australia Pty Ltd.) pelletised formulation containing 60 g/kg Iron(III)-EDTA Complex. DEFENDER as well as MULTICROP MULTIGUARD® are commercially available in Australia and used for the control of the common garden snail *Helix aspersa*.

Each plot consisted of a 20 cm high galvanised sheet material ring (ground surface area of 1.13 m$^2$) covered with a green nylon shade cloth (50% shade rated). Twelve lettuce seedlings were planted evenly within each plot prior to treatment application. The plots were watered as required with the same volume of water per plot using a hand held rose sprinkler head. Two shelters in form of black plastic pots were placed within the plots to provide harbourage for snails.

After the lettuce seedlings were transplanted and during late afternoon when sunlight was mild granulates were evenly distributed manually to respective plots from plastic containers used to weigh the required quantity of each treatment per plot.

In the centre of each plot 10 *Helix aspersa* snails were placed within 10 minutes after distribution of granulates.

At each assessment the plots were checked to make sure that granulates remained available to the snails. Efficacy post-treatment assessments were conducted at 1, 4, 7 and 14 days (days after treatment—DAT). Snails were assessed as active, knocked down or dead at each assessment, similarly as in Examples I and II. The percentage snail mortality (knocked down and dead) was calculated for each treatment replicate. The mean percentage of lettuce seedlings leaf area consumed and the mean number of lettuce seedlings damaged was calculated for each assessment.

Tables III.1, III.4 and III.3 show the results of the tests.

TABLE III.1

Mean Percentage Snail Mortality

| | | Mean Percentage Snail Mortality (Snails Knocked Down and Dead/All snails) | | | |
|---|---|---|---|---|---|
| Granulate | Amount [g/m$^2$] | 1 DAT | 4 DAT | 7 DAT | 14 DAT |
| E (Example II) | 5.0 | 77.1 | 88.6 | 98.6 | 97.1 |
| A (Example I) | 5.0 | 2.9 | 44.3 | 61.4 | 70.0 |
| DEFENDER | 5.0 | 71.4 | 64.3 | 70.0 | 67.1 |
| MULTIGUARD | 5.0 | 12.9 | 80.0 | 84.3 | 84.3 |
| Untreated | 0.0 | 0.0 | 0.0 | 0.0 | 0.0 |

TABLE III.2

Mean Percentage of Lettuce Seedlings Leaf Area Consumed

| | | Mean Percentage of Lettuce Seedlings Leaf Area Consumed | | | |
|---|---|---|---|---|---|
| Granulate | Amount [g/m$^2$] | 1 DAT | 4 DAT | 7 DAT | 14 DAT |
| E (Example II) | 5.0 | 0.01 | 0.2 | 0.2 | 0.2 |
| A (Example I) | 5.0 | 0.1 | 0.1 | 0.1 | 1.4 |

TABLE III.2-continued

Mean Percentage of Lettuce Seedlings Leaf Area Consumed

| Granulate | Amount [g/m²] | Mean Percentage of Lettuce Seedlings Leaf Area Consumed | | | |
|---|---|---|---|---|---|
| | | 1 DAT | 4 DAT | 7 DAT | 14 DAT |
| DEFENDER | 5.0 | 0.04 | 0.2 | 0.2 | 1.4 |
| MULTIGUARD | 5.0 | 0.1 | 0.1 | 0.1 | 0.4 |
| Untreated | 0.0 | 0.96 | 3.4 | 3.7 | 16.8 |

TABLE III.3

Mean Number of Lettuce Seedlings Damaged

| Granulate | Amount [g/m²] | Mean Number of Lettuce Seedlings Damaged | | | |
|---|---|---|---|---|---|
| | | 1 DAT | 4 DAT | 7 DAT | 14 DAT |
| E (Example II) | 5.0 | 0.1 | 0.6 | 0.6 | 0.6 |
| A (Example I) | 5.0 | 0.4 | 0.6 | 0.6 | 0.7 |
| DEFENDER | 5.0 | 0.3 | 0.6 | 0.6 | 1.4 |
| MULTIGUARD | 5.0 | 0.6 | 0.6 | 0.7 | 0.9 |
| Untreated | 0.0 | 2.7 | 4.4 | 4.6 | 6.3 |

In trials granulate A (EDTA acid, iron powder, without humic acid) has proved to be the slowest compared with other formulations and the final percentage mortality for the granulate A after 14 days ranged only to 70.0%.

On the other hand granulate E (EDTA acid, iron powder with humic acid) proved to be the fastest and the most efficient. Granulate E also unexpectedly not resulted in damaged or consumed lettuce seedlings. This effect may be attributed to high palatability of granulate E due to the content of the humic acid.

Above mentioned results proved that composition E according to the invention is an effective and ecological alternative to formulations containing metaldehyde, toxic molluscicidal agent harmful to dogs and other domestic animals.

What is claimed is:

1. A molluscicide composition against terrestrial mollusks having a form of food bait and comprising at least one molluscicidal agent selected from the group consisting of metaldehyde, methiocarb, iron powder plus ethylenediaminetetraacetic acid (EDTA), methylglycinediacetic acid (MGDA) and/or mixtures thereof in all ratios, characterized in that it further comprises a humic substance, wherein the humic substance consists of a humic acid, which is not soluble in water under acidic conditions, in an amount from 1 to 30% by weight of the composition, wherein said composition is substantially free of fulvic acid.

2. The molluscicide composition according to claim 1, characterised in that said molluscicidal agents include EDTA acid and iron powder.

3. The molluscicide composition according to claim 2, characterised in that it contains up to 10% by weight of EDTA acid and up to 5% by weight of iron powder, preferably from 2 to 5% by weight of EDTA acid and from 0.5 to 2% by weight of iron powder.

4. The molluscicide composition according to claim 1, characterised in that it further comprises plant materials containing starch, preferably wheat or corn meal or potato starch or mixtures thereof in all ratios.

5. The molluscicide composition according to claim 1, characterised in that it further comprises one or more of the following constituents:
   a. substances against mould growth, such as IPBC, DCOIT and/or sorbic acid;
   b. alerting (aversive) agents, such as denatonium benzoate;
   c. rain-resistance improving agents;
   d. granulate extrusion process improving agents, such as kaolinite and/or modified starch;
   e. synthetic or natural fertilizers, such as urea and/or humus;
   f. additional attractants, such as red clover, yeast, sugar, paraldehyde, isoamyl acetate, 2-methyldecanol, and/or sulfur compounds.

6. The molluscicide composition according to claim 1, characterised in that it has a form of a grain, a pellet, a granule, a powder, a capsule and a paste, with a pellet and a granule being more preferred.

7. A method of preparing a molluscicidal composition as defined in claim 1, characterised in that the components are mixed and the mixture is appropriately converted to form a grain, a pellet, a granule, a powder, a capsule and a paste, with a pellet and a granule being more preferred.

8. A molluscicide dosage form comprising the molluscicide composition as defined in claim 1, characterised in that the dosage form is selected from the group consisting of a grain, a pellet, a granule, a powder, a capsule and a paste, with a pellet and a granule being more preferred.

9. A method for mollusc control, in which the molluscicide composition as defined in claim 1 or the molluscicide dosage form as defined in claim 8 is applied to a field infested, or likely to become infested, with molluscs, over the entire field or only in the specified centers of molluscs' occurrence, wherein the application is optionally repeated during the season as necessary.

10. The method according to claim 9, in which composition as defined in claim 1 or molluscicide dosage form as defined in claim 8 is applied in an amount of 0.1 g/m2 to 10 g/m2, preferably in the form of pellets and/or granules.

* * * * *